US012781178B2

(12) United States Patent
Dupuis et al.

(10) Patent No.: US 12,781,178 B2
(45) Date of Patent: Nov. 3, 2026

(54) STRUCTURING A SET OF OBJECTS SUCH AS CELLS AND MICRON-SIZED PARTICLES USING ACOUSTIC FORCE

(71) Applicants: CENTRE NATIONAL DE LA RECHERCHE SCIENTIFIQUE, Paris (FR); ECOLE SUPERIEURE DE PHYSIQUE ET DE CHIMIE INDUSTRIELLES DE LA VILLE DE PARIS, Paris (FR); INSTITUT NATIONAL DE LA SANTE ET DE LA RECHERCHE MEDICALE, Paris (FR); SORBONNE UNIVERSITE, Paris (FR); UNIVERSITE PARIS CITE, Paris (FR)

(72) Inventors: Chloé Dupuis, Paris (FR); Jean-Luc Aider, Vanves (FR); Jean-Michel Peyrin, Paris (FR); Mauricio Hoyos, Creteil (FR)

(73) Assignees: CENTRE NATIONAL DE LA RECHERCHE SCIENTIFIQUE, Paris (FR); ECOLE SUPERIEURE DE PHYSIQUE ET DE CHIMIE INDUSTRIELLES DE LA VILLE DE PARIS, Paris (FR); INSTITUT NATIONAL DE LA SANTE ET DE LA RECHERCHE MEDICALE, Paris (FR); SORBONNE UNIVERSITE, Paris (FR); UNIVERSITE PARIS CITE, Paris (FR)

( * ) Notice: Subject to any disclaimer, the term of this patent is extended or adjusted under 35 U.S.C. 154(b) by 301 days.

(21) Appl. No.: 18/694,769

(22) PCT Filed: Sep. 27, 2022

(86) PCT No.: PCT/EP2022/076869
§ 371 (c)(1),
(2) Date: Mar. 22, 2024

(87) PCT Pub. No.: WO2023/052370
PCT Pub. Date: Apr. 6, 2023

(65) Prior Publication Data

US 2025/0115862 A1 Apr. 10, 2025

(30) Foreign Application Priority Data

Sep. 28, 2021 (FR) ...................................... 2110209

(51) Int. Cl.
*C12M 1/00* (2006.01)
*C12M 1/12* (2006.01)

(52) U.S. Cl.
CPC ............ *C12M 47/04* (2013.01); *C12M 25/14* (2013.01); *C12M 47/20* (2013.01)

(58) Field of Classification Search
CPC ...... C12M 25/14; C12M 25/16; C12M 47/04; C12M 47/20
See application file for complete search history.

(56) References Cited

U.S. PATENT DOCUMENTS 4,983,189 A * 1/1991 Peterson ................ B01D 43/00 366/127
5,225,089 A * 7/1993 Benes .................... B01D 43/00 366/127

(Continued)

FOREIGN PATENT DOCUMENTS

JP 2009288060 A * 12/2009
WO 2019071039 A1 4/2019

(Continued)

OTHER PUBLICATIONS

International Search Report issued on Feb. 3, 2022, in corresponding International Application No. PCT/ EP2022/076869, 6 pages.

(Continued)

*Primary Examiner* — Natalie Huls

(74) *Attorney, Agent, or Firm* — Maier & Maier, PLLC

(57) ABSTRACT

A technique for moving various objects such as cells and particles of hydrogel or a compressible material, suspended in a fluid, so as to form a layered structure akin to human organ tissue. A standing sound wave is propagated through the fluid so as to position the cells on a pressure node and the particles on a pressure antinode. As such, the cells have a positive acoustic contrast relative to the fluid, while the particles have a negative acoustic contrast relative to the fluid.

8 Claims, 4 Drawing Sheets

(56) References Cited

U.S. PATENT DOCUMENTS

| | | | | |
|---|---|---|---|---|
| 8,083,068 | B2 | 12/2011 | Kaduchak et al. | |
| 2015/0118692 | A1* | 4/2015 | Johnson | G01N 33/545 435/7.1 |
| 2017/0217794 | A1* | 8/2017 | Lipkens | C12N 1/02 |
| 2017/0304746 | A1* | 10/2017 | Lipkens | B01D 17/06 |
| 2018/0186107 | A1* | 7/2018 | Buchanan | B29C 70/62 |
| 2018/0223439 | A1* | 8/2018 | Lipkens | C25B 1/13 |
| 2018/0361053 | A1* | 12/2018 | Fiering | B01L 3/50273 |
| 2019/0076769 | A1* | 3/2019 | Meacham | B01D 43/00 |
| 2023/0273157 | A1* | 8/2023 | Oswald | G01N 29/4436 435/29 |
| 2025/0183024 | A1* | 6/2025 | Ray | H01J 49/4225 |

FOREIGN PATENT DOCUMENTS

| | | | |
|---|---|---|---|
| WO | 2020232370 | A1 | 11/2020 |
| WO | 2020245432 | A1 | 12/2020 |

OTHER PUBLICATIONS

Search Report issued on May 11, 2022, in corresponding French Application No. 2110209, 2 pages.

Bouyer et al., "A Bio-Acoustic Levitational (BAL) Assembly Method for Engineering of Multilayered, 3D Brain-Like Constructs, Using Human Embryonic Stem Cell Derived Neuro-Progenitors", Advanced Materials, 2016, 28, 161-167, 7 pages.

Yin et al., "Effective Cell Trapping using PDMS Microspheres in an Acoustofluidic Chip", Colloids and Surfaces B: Biointerfaces, Elsevier B.V., Jun. 9, 2017, vol. 157, 9 pages.

* cited by examiner

STRUCTURING A SET OF OBJECTS SUCH AS CELLS AND MICRON-SIZED PARTICLES USING ACOUSTIC FORCE

TECHNICAL FIELD

The invention relates to the field of biotechnology and in particular to structuring of cellular assemblies, for example with a view to reconstructing or modelling living tissues. The invention is of particular, but in no way limiting, interest in the sectors of cell therapy, pharmacological modelling, agri-foodstuff, for example for the cultivation of meat, micro-algae or plants, or even aerospace, in particular for cell cultivation under microgravity conditions.

BACKGROUND

In the context of research into the reconstruction and modelling of organ-on-a-chip and organoids, a growing number of experimental approaches are aimed at structuring cellular assemblies.

The techniques most commonly used for this purpose include manipulation of cells within microfluidic devices and formation of tissues by additive manufacturing.

Another well-known technique, described in the following paper, consists in structuring cells using acoustic levitation: Bouyer et al. A *bio-Acoustic Levitational* (*BAL*) *Assembly Method for Engineering of Multilayered,* 3D *Brain-Like Constructs, Using Human Embryonic Stem Cell Derived Neuro-Progenitors, Adv. Mater.* 2016, 28, 161-167. This technique makes it possible to structure layered cells with the aim of establishing connections between cells in different layers, but does not make it possible to satisfactorily control development of such connections.

Generally speaking, known techniques in this field are complex and costly, can require long periods of time to structure and culture cells and, when implemented in vitro, can lead to the death of a large number of cells.

SUMMARY

In order to overcome the aforementioned drawbacks, the present invention provides a method for structuring a set of objects, comprising:

- a step of arranging a fluid and said objects suspended in the fluid in a cavity, and
- a step of generating a stationary acoustic wave in the cavity so as to produce an acoustic radiation force causing the objects to move in the cavity, said objects comprising:
  - first objects which have a positive acoustic contrast with respect to the fluid, and
  - second objects which have a negative acoustic contrast with respect to the fluid.

Propagation of a stationary acoustic wave in the cavity makes it possible to form in the cavity, along the direction of propagation, one or more nodes, that is places where the pressure of the fluid is zero, and one or more antinodes, that is places where this pressure is at a maximum.

Since the first objects have a positive acoustic contrast, that is a positive density-compressibility factor, relative to the fluid, they will be transported by the acoustic radiation force towards a pressure node. The second objects, on the other hand, have a negative acoustic contrast, or density-compressibility factor, and will be transported by the acoustic radiation force towards a pressure antinode.

The invention thus makes it possible to form, in the cavity, one or more aggregates of first objects and one or more aggregates of second objects as layers, or foils, which succeed one another along the direction of propagation, in an extremely rapid manner—typically in a few seconds—and using equipment that is particularly simple to implement and inexpensive.

Such a layered structure resembles the structure of human organ tissues, which typically comprise layers of cells separated by layers of an extracellular matrix. For example, epithelia, especially cardiac, pulmonary or endothelial epithelia, may comprise differentiated or undifferentiated layers which in a number of cases rest on basal laminae of a protein nature, for example epithelial or muscle cells. As another example, the blood-brain barrier or brain parenchyma typically comprise layers of interconnected neurons.

In addition, the invention makes it possible to maintain all the objects structured in this way in acoustic levitation, under the action of the stationary acoustic wave, the generation of which can be maintained for the required period of time, for example several hours or days, in order to promote interactions between objects when these are alive, in particular when they are formed by biological cells.

The invention thus makes it possible to produce a cell culture in acoustic levitation, by controlling permeability and as a result development of connections and interactions between layers of cells forming the first objects, by choosing second objects forming one or more layers of selected porosity.

This innovative approach also makes it possible to limit contact between the objects and walls or surfaces, thereby preserving their mechanical and functional integrity.

In the present description, an "object" refers to a living or inert element that is preferably small in size compared to the length of the acoustic wave generated in the cavity.

By way of a non-limiting example, the objects can typically be micrometric in size, for example between 1 μm and 100 or several hundred μm.

Thus, in a preferred but in no way limiting embodiment, said first objects are living elements such as biological cells, for example of the eukaryotic or prokaryotic type.

Said second objects may be inert elements such as particles comprising a hydrogel, for example based on collagen, gelatin, or fibrin and extracellular matrix protein. As a non-limiting alternative, the second objects may comprise a compressible elastomer, for example polydimethylsiloxane.

However, the invention can be implemented with objects of a different size, that is outside the aforementioned range.

Thus, the objects or some of them may be smaller than 1 μm, being formed for example by bacteria or viruses, and/or several hundred μm in size.

The objects, especially the first objects, or some of them, may be multicellular elements or artificially formed objects or even objects taken from an organ.

The fluid in which the objects are suspended is preferably a liquid which, depending on the application contemplated, may comprise water or form a culture medium.

The invention thus provides a simple solution for reconstituting artificial tissues for research purposes or as part of cellular therapies.

The invention also provides a particularly precise solution in terms of positioning objects in space and, if necessary, controlling the development of intercellular interactions.

The simplicity and precision of this technique are due in particular to the limited number of control parameters, namely the respective density and sound wave propagation velocity of the fluid and the objects, as well as the velocity and frequency of the acoustic wave.

Of course, many alternatives can be implemented on the basis of the principle described above.

For example, other objects can be injected into the fluid after the first and second objects have been positioned, so as to form additional or complementary aggregates, for example.

In one particular embodiment, the stationary acoustic wave generated in the cavity has a wavelength less than twice a dimension of the cavity along a direction of propagation of the stationary acoustic wave.

Preferably, this wavelength is less than or equal to this dimension.

It is preferred that the stationary acoustic wave has at least one antinode and at least one or two nodes.

In the scope of a favoured alternative embodiment, this makes it possible to form two layers of first objects separated by a layer of second objects.

In particular in the context of such an alternative, the use of hydrogel or compressible elastomer to form the second objects makes it possible to constitute a porous intermediate layer, affording development of interactions between the layers of first objects extending on either side of this intermediate layer, when the first objects comprise living cells.

The invention not only makes it possible to carry out cell culture using acoustic levitation but also, alternatively or additionally, to initiate or continue such a process by holding the objects in position using a matrix.

Especially, the method can comprise, after positioning the objects under the action of the acoustic radiation force, a step of introducing a substance into the cavity so as to form a matrix capable of supporting the first objects.

This substance is preferably a biocompatible active substance promoting phase change of the medium constituted by the fluid.

This substance may comprise a hydrogel prepolymer or another element capable of forming a matrix in gel form.

The substance may comprise a catalyst and/or a photoinitiator.

A matrix in gel form allows the objects to be adequately held in position in space whilst being elastically deformable.

Additionally it is preferred that the matrix is porous, whether it is in gel form or in another form.

The porosity of the matrix makes it permeable and perfusable, so as to afford development of cellular connections.

In one alternative embodiment, said substance comprises a photopolymerisable material, the method comprising, after introducing the substance into the cavity, a step of light stimulating the substance so as to polymerise it.

The invention thus makes it possible to shape a support matrix for the structured set of objects, in particular the first objects.

In the scope of the various alternatives just described, the method may comprise a step of incubating the objects after they have been positioned under the action of the acoustic radiation force.

For example, the cavity and its contents can be placed in an incubator for this purpose.

Incubation promotes differentiation, self-organisation and maturation of cell layers. In one embodiment, the method comprises, after positioning the objects under the action of the acoustic radiation force, a step of heating the second objects so as to melt them.

The heating step can be carried out using a laser sheet.

When a support matrix as described above is resorted to, such a heating step is preferably carried out before the matrix is formed.

In one embodiment, the method comprises, after positioning the objects under the action of the acoustic radiation force, a step of encapsulating the first objects.

Preferably, this encapsulation step comprises introducing third objects with a positive acoustic contrast relative to the fluid into the cavity.

The third objects can thus be transported by the acoustic radiation force towards a pressure node to form a protective shell around the first objects located therein.

By way of example, the third objects may comprise hydrogel beads or another material for forming a porous protective shell.

The encapsulation step is preferably, but not necessarily, implemented when a supporting matrix is not resorted to.

The invention can also be implemented for cell therapy purposes, for example by in vivo injection of a culture or proto-culture produced using the principles described herein. Further advantages and characteristics of the invention will become apparent from the following detailed, non-limiting description.

BRIEF DESCRIPTION OF THE DRAWINGS

The following detailed description refers to the attached drawings in which.

DETAILED DESCRIPTION

Figure 1:
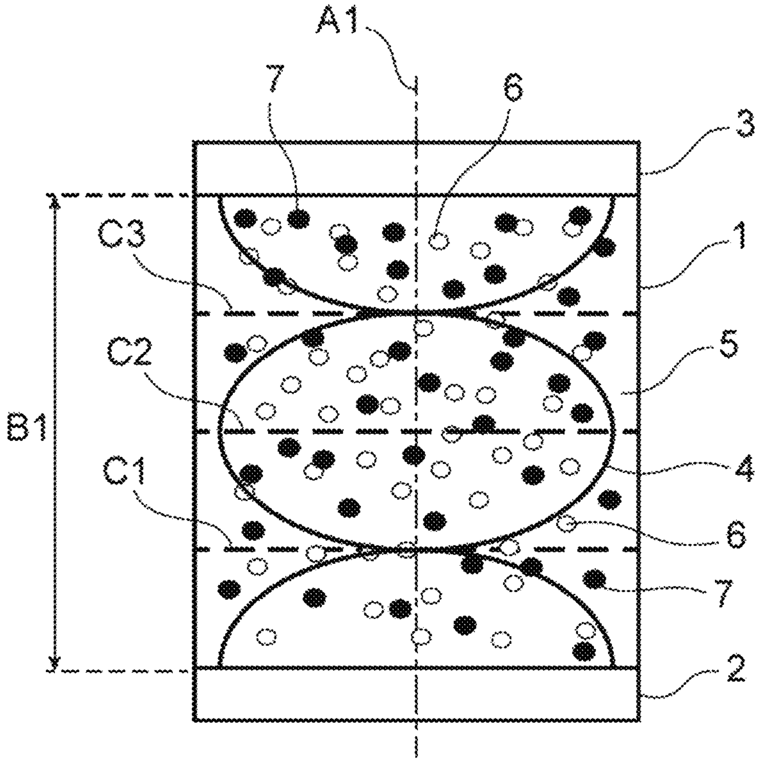
FIG. 1 is a schematic view of a device comprising a cavity and a transducer capable of generating a stationary acoustic wave in the cavity, the cavity containing a fluid with suspended objects which are relatively homogeneously distributed in the cavity before undergoing the effects of the acoustic wave.
Figure 2:
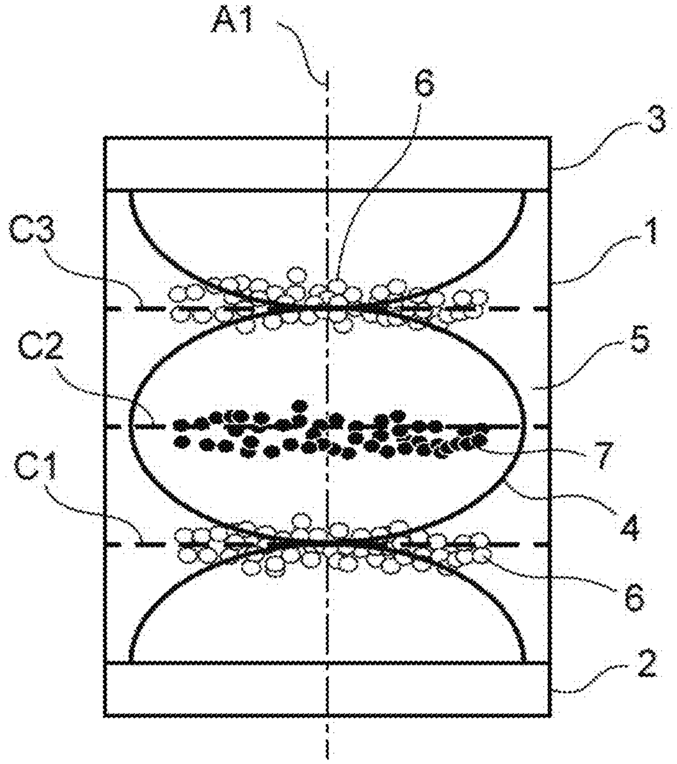
FIG. 2 is a schematic view of the device of FIG. 1, in which the objects have been moved by an acoustic radiation force produced by the acoustic wave so as to be aligned on a node or an antinode of this wave respectively.

FIGS. 1 and 2 represent a device for implementing the invention.

This device comprises, on the one hand, a container which forms a cavity 1 capable of containing a fluid and/or different substances in the form of a liquid or gel, for example.

Generally speaking, the cavity 1 extends along a direction A1, which in this example corresponds to a vertical direction. The cavity 1 has a dimension B1 along direction A1, which in this example corresponds to the height of the cavity 1.

The cavity 1 has an overall cylindrical shape. Of course, cavity 1 may have another geometry, for example a rectangular cross-section.

On the other hand, the device of FIGS. 1 and 2 comprises an acoustic wave generation system.

In this example, this system comprises a piezoelectric transducer 2 arranged at a first end of the cavity 1 along direction A1, in this case vertically below the cavity 1, as well as an acoustic reflector 3 which delimits a second end of the cavity 1 along direction A1, in this case being arranged vertically above the cavity 1.

This system is configured so as to be able to generate in cavity 1 and propagate in the fluid it contains a stationary acoustic wave 4, along a direction of propagation corresponding to direction A1.

The stationary wave 4 generated in this way can have a frequency identical to the resonant frequency of the cavity 1, which consequently forms a resonator.

Alternatively, this stationary wave 4 may have a frequency different from the resonant frequency of the cavity 1.

In any case, the system is configured to be able to generate, especially, a wave 4 having a wavelength A less than or equal to twice the height B1 of the cavity 1, in order to form at least one pressure node and at least one pressure antinode along direction A1.

In this example, the transducer 2 is a broadband transducer equipped with an ultrasound source.

Such a transducer 2 makes it possible to modify position of the node or nodes of the wave 4 along direction A1 and/or the distance between different nodes of the wave 4, by varying the frequency of this wave 4.

In the scope of the invention, the device just described, or any similar device, is implemented to position small-sized, typically micro-sized, objects within the cavity 1 in a spatial organisation determined by one or more parameters of the wave 4, in particular its frequency.

Indeed, the cavity 1 is filled with a fluid 5 and objects 6 and 7 suspended in this fluid 5.

In this non-limiting example, the objects 6 are biological cells, the fluid 5 forms a culture medium for these cells 6 and the objects 7 are polydimethylsiloxane beads.

By way of indicating purposes, each of the objects 6 and 7 is between 1 μm and 100 μm in size and the height B1 of the cavity 1 is several centimetres.

In this example, each of the objects 6 has a density $\rho_{o1}$ greater than the density $\rho_f$ of the fluid 5. Conversely, each of the objects 7 has a density $\rho_{o1}$ less than the density pf of the fluid 5.

The objects 6 are also chosen so that the velocity $c_{o1}$ of propagation of an acoustic wave in these objects 6 is greater than the velocity $c_f$ of propagation of this acoustic wave in the fluid 5. Conversely, the objects 7 are chosen so that the velocity $c_{o2}$ of propagation of the acoustic wave in these objects 7 is less than the velocity $c_f$ of propagation of this acoustic wave in the fluid 5.

After arranging the fluid 5 in the cavity 1 and the objects 6 and 7 suspended in the fluid 5 as illustrated in FIG. 1, the transducer 2 is actuated so as to generate a stationary acoustic wave 4 in the cavity 1.

The generation of this wave 4 makes it possible to produce an acoustic radiation force which is exerted on the objects 6 and 7.

This acoustic radiation force FRA can be described in particular according to the following model, known per se, by K. Yosioka and Y. Kawasima:

$$FRA = \frac{\pi}{8}\rho_f v_0^2 k d^3 F_y \sin(kz)$$

where $v_0$ is the velocity of wave 4, k the wavenumber, $F_y$ a density-compressibility factor and z the position of the object 6 or 7 under consideration along direction A1, that is along the direction of propagation of the wave 4.

The density-compressibility factor $F_y$ can be defined as follows:

$$F_y = \frac{1 + \frac{2}{3}\left(1 - \frac{\rho_f}{\rho_{ox}}\right)}{2 + \frac{\rho_f}{\rho_{ox}}} - \frac{\rho_f c_f^2}{3\rho_{ox} c_{ox}^2}$$

where $\rho_{ox}$ is the density $\rho_{o1}$ or $\rho_{o2}$ of the object 6, or respectively 7, under consideration, and cox is the velocity $c_{o1}$ or $c_{o2}$ of propagation of the wave 4 within the object 6, or respectively 7, under consideration.

Given the respective density and the respective velocity of propagation of the acoustic wave of objects 6 and 7 relative to the fluid 5, objects 6 have a positive density-compressibility factor, or acoustic contrast, while objects 7 have a negative density-compressibility factor, or acoustic contrast.

In the example of FIGS. 1 and 2, the wave 4 has a wavelength λ equal to height B1 of the cavity 1, forming respectively along direction A1, a first node at a coordinate C1, an antinode at a coordinate C2 and a second node at a coordinate C3.

Given the aforementioned respective properties of the fluid 5 and the objects 6 and 7, starting from the configuration of FIG. 1 in which the objects 6 and 7 are relatively homogeneously distributed throughout the cavity 1, the acoustic radiation force produced by the wave 4 thus causes the objects 6 to move towards the nodes of the wave 4 and the objects 7 to move towards the antinode of the wave 4, so as to achieve a configuration such as that illustrated in FIG. 2.

The invention thus makes it possible to spatially organise the objects 6 and 7 as layers spaced along direction A1 and to keep them thus positioned in acoustic levitation, under the action of the wave 4.

In this example, the objects 7 form an intermediate layer, located halfway up the cavity 1, while the objects 6 form two layers extending on either side of the intermediate layer.

As the objects 7 are polydimethylsiloxane beads, their aggregation or pooling as a layer makes it possible to constitute a porous barrier which affords interactions to develop between the layers of cells 6, without any contact with the walls of the cavity 1.

The invention thus makes it possible to produce a cell culture with acoustic levitation.

The invention also makes it possible to control interactions between layers of cells 6, since it is especially possible to choose different materials, geometries and sizes for the objects 7, these parameters having a direct effect on the porosity of the barrier they constitute under the action of the acoustic radiation force.

Figure 3:
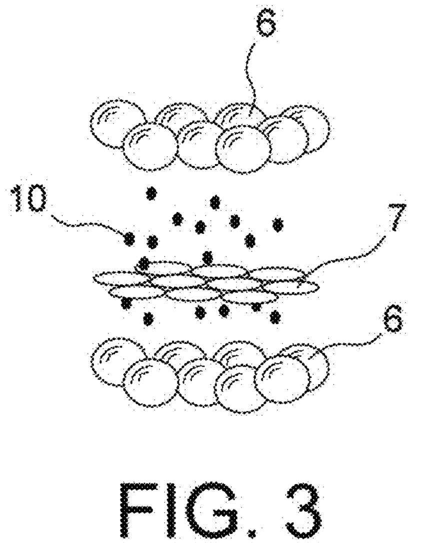
FIG. 3 is a schematic view illustrating a phenomenon of diffusion between layers of cells.
Figure 4:
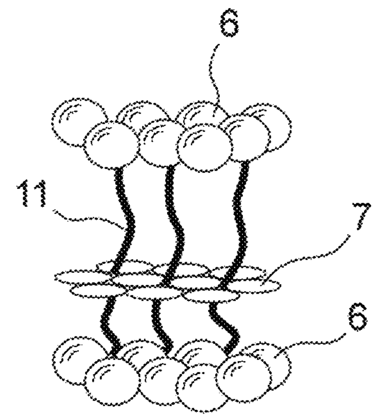
FIG. 4 is a schematic view illustrating a phenomenon of development of cell extensions.
Figure 5:
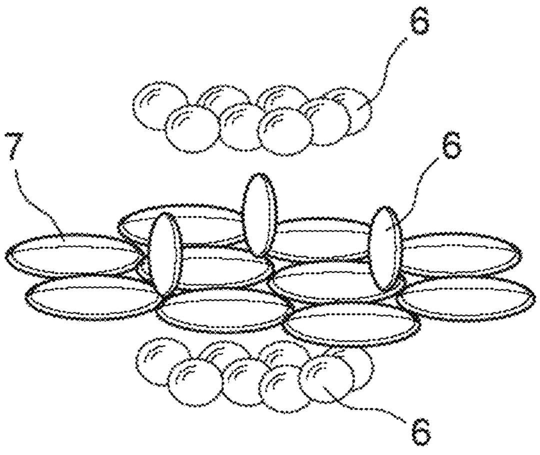
FIG. 5 is a schematic view illustrating a phenomenon of cell migration.

By way of example, it is thus possible to trigger or afford diffusion of solutes or cell secretion product 10 (FIG. 3), the development of cellular extensions 11 of the neuronal axon type (FIG. 4), or even the migration of cells 6 (FIG. 5).

In one alternative embodiment, the objects 7 comprise hydrogel particles which, after positioning under the action of the acoustic radiation force as described below, are molten by local heating, for example using a laser sheet.

It is thus possible to constitute a continuous hydrogel layer interposed between two layers of cells 6.

The invention also makes it possible to continue cell culture, or to initiate it after positioning the objects 6 and 7 as described above, by producing a support matrix in the cavity 1.

To do this, once the objects 6 and 7 have been positioned in the configuration of FIG. 2 or in a similar configuration, a hydrogel prepolymer-based substance can be introduced into cavity 1.

Figure 6:
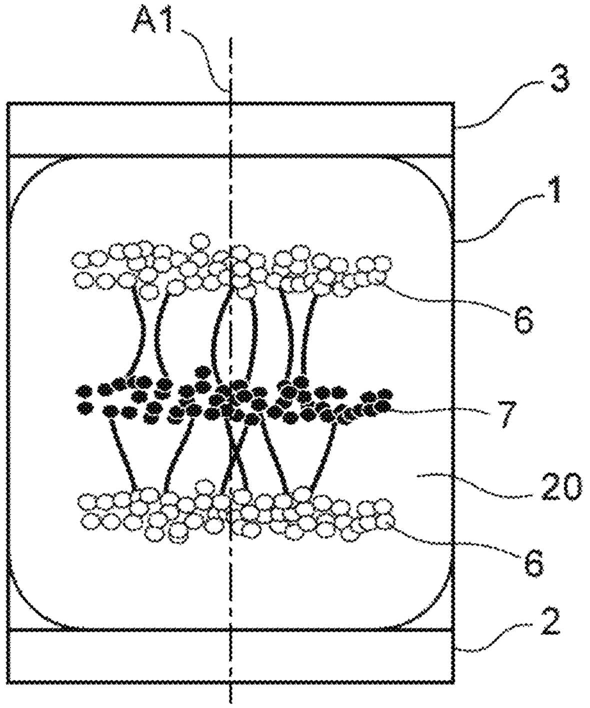
FIG. 6 is a schematic view of the device of FIG. 2, the objects being held in the configuration of FIG. 2 by means of a gel matrix.

Such a substance makes it possible to constitute a porous matrix 20 as a gel, making it possible to support the layers of objects 6 and 7 (FIG. 6).

In one embodiment, this substance also comprises a photopolymerisable material which, after introduction into cavity 1, is subjected to light stimulation leading to polymerisation of the matrix.

The acoustic wave 4 can then be interrupted so that cell culture occurs within such a matrix, for example by placing the container in an incubator.

In one alternative embodiment, starting from the configuration of FIG. 2, other objects (not represented) such as positive acoustic contrast hydrogel beads are introduced into the cavity 1.

Under the action of the acoustic radiation force resulting from wave 4, these beads or any other objects with positive acoustic contrast will move towards the pressure nodes so as to envelop layers formed by the objects 6.

It is thus possible to encapsulate the layers of objects 6 using a shell with a porosity controlled by the properties of the objects that form it, for example for in vivo cell therapy applications.

It follows from the above non-limiting description that the invention makes it possible to reconstruct and stimulate complex architectures including different layers of cells separated by a variety of objects making it possible to control interactions between the cell layers, using a method and a device that are particularly simple to implement.

The invention claimed is:

1. A method for structuring a set of objects, comprising:

arranging a fluid and said objects suspended in the fluid in a cavity;

generating a stationary acoustic wave in the cavity so as to produce an acoustic radiation force causing the objects to move in the cavity;

wherein said objects comprise:

first objects which have a positive acoustic contrast with respect to the fluid, and second objects which have a negative acoustic contrast with respect to the fluid, wherein the stationary acoustic wave is held so as to keep the objects thus moved in acoustic levitation, and wherein, after positioning the objects under the action of the acoustic radiation force, the method comprises introducing a substance into the cavity so as to form a matrix capable of supporting the first objects.

2. The method according to claim 1, wherein the stationary acoustic wave generated in the cavity has a wavelength less than twice a dimension of the cavity along a direction of propagation of the stationary acoustic wave.

3. The method according to claim 1, wherein said substance comprises a hydrogel prepolymer.

4. The method according to claim 1, wherein the matrix is porous.

5. The method according to claim 1, wherein said substance comprises a photopolymerisable material, the method comprising, after introducing the substance into the cavity, a step of light stimulating the substance so as to polymerise it.

6. The method according to claim 1, comprising, after positioning the objects under the action of the acoustic radiation force, a step of incubating the objects.

7. The method according to claim 1, comprising, after positioning the objects under the action of the acoustic radiation force, a step of heating the second objects so as to melt them.

8. The method according to claim 1, comprising, after positioning the objects under the action of the acoustic radiation force, a step of encapsulating the first objects, this step comprising introducing third objects having a positive acoustic contrast with respect to the fluid into the cavity.

* * * * *